United States Patent
Costantino (10) Patent No.: US 6,706,041 B1
(45) Date of Patent: Mar. 16, 2004

(54) HOLDERS FOR ABLATION DEVICES, SURGICAL DEVICES EMPLOYING SUCH HOLDERS, AND METHODS OF EMPLOYING SUCH SURGICAL DEVICES

(76) Inventor: Peter Costantino, 12 Wrights Mill Rd., Armonk, NY (US) 10504

( * ) Notice: Subject to any disclaimer, the term of this patent is extended or adjusted under 35 U.S.C. 154(b) by 62 days.

(21) Appl. No.: 10/051,112

(22) Filed: Jan. 22, 2002

Related U.S. Application Data (60) Provisional application No. 60/312,431, filed on Aug. 15, 2001.

(51) Int. Cl.$^7$ .............................................. A61B 18/18
(52) U.S. Cl. ............................. 606/41; 604/35; 606/45
(58) Field of Search ............................. 606/41, 45, 46, 606/48–50, 15–17; 604/35

(56) References Cited

U.S. PATENT DOCUMENTS

| | | | | |
|---|---|---|---|---|
| 4,985,027 A | * | 1/1991 | Dressel ......................... | 606/15 |
| 5,195,958 A | * | 3/1993 | Phillips ......................... | 604/33 |
| 5,197,963 A | * | 3/1993 | Parins .......................... | 606/46 |
| 5,366,443 A | | 11/1994 | Eggers et al. | |
| 5,460,602 A | * | 10/1995 | Shapira ......................... | 604/22 |
| 5,681,282 A | | 10/1997 | Eggers et al. | |
| 5,697,281 A | | 12/1997 | Eggers et al. | |
| 5,697,882 A | | 12/1997 | Eggers et al. | |
| 5,697,909 A | | 12/1997 | Eggers et al. | |
| 5,725,524 A | * | 3/1998 | Mulier et al. .................. | 606/41 |
| 5,871,469 A | | 2/1999 | Eggers et al. | |
| 6,063,081 A | | 5/2000 | Mulier et al. | |
| 6,152,919 A | * | 11/2000 | Hakky ......................... | 606/15 |
| 6,238,393 B1 | | 5/2001 | Mulier et al. | |
| 6,277,115 B1 | | 8/2001 | Saadat | |
| 6,355,034 B2 | * | 3/2002 | Cosmescu ..................... | 606/45 |
| 2003/0069572 A1 | * | 4/2003 | Wellman et al. .............. | 606/41 |

* cited by examiner

Primary Examiner—Michael F. Peffley
(74) Attorney, Agent, or Firm—Baker Botts L.L.P.

(57) ABSTRACT

A holder for an ablation device includes an inner cavity having a first opening formed therethrough, in which the inner cavity is adapted to receive an ablation device. In an embodiment, the holder may include a first outer cavity surrounding the inner cavity. In another embodiment, the holder may include a tip portion having a second opening formed therethrough, in which the tip portion is formed at a first end of the holder and extends beyond the inner cavity, such that a reaction chamber is formed between the first opening and the second opening. A surgical device includes a holder for an ablation device, which includes an inner cavity having a first opening formed therethrough, in which the inner cavity is adapted to receive an ablation device. The surgical device also includes an ablation device disposed within the inner cavity. In an embodiment, the holder may include a first outer cavity surrounding the inner cavity. In another embodiment, the holder may include a tip portion having a second opening formed therethrough, in which the tip portion is formed at a first end of the holder and extends beyond the inner cavity, such that a reaction chamber is formed between the first opening and the second opening.

44 Claims, 6 Drawing Sheets

HOLDERS FOR ABLATION DEVICES, SURGICAL DEVICES EMPLOYING SUCH HOLDERS, AND METHODS OF EMPLOYING SUCH SURGICAL DEVICES

This application claims priority from U.S. Provisional Patent Application No. 60/312,431, filed on Aug. 15, 2001, and entitled "Safety Tip and Reaction Chamber for an Electrosurgical Probe," the disclosure of which is incorporated herein by reference in its entirety.

BACKGROUND OF THE INVENTION

1. Field of the Invention

The invention relates generally to the field of surgical devices and methods of employing such surgical devices. More specifically, the invention is directed towards holders for ablation devices, surgical devices employing such holders, and methods of employing such surgical devices.

2. Description of Related Art

An ablation device may be used during a surgical procedure in order to ablate e.g., amputate or otherwise reduce or dissipate a patient's body part, tissue, or the like. Some known ablation devices may use radio frequency (RF) to create a charge of electricity in order to ablate the patient's tissue. For example, with some known ablation devices, a tip of the ablation device may contact the patient's tissue, which may ablate the patient's tissue. With other known ablation devices, a conductive fluid may be sprayed onto the target site via the tip of the ablation device. As such, the charge of electricity may be applied from the tip of the ablation device to the patient's tissue via the conductive fluid, which may allow the tip of the ablation device to ablate the patient's tissue without directly contacting the patient's tissue.

Nevertheless, with such known ablation devices, when the tip of the ablation device contacts the patient's tissue, the ablation device may ablate portions of the patient's tissue which the user of the ablation device did not intend or desire to ablate. Similarly, when conductive fluid irrigates portions of the patient's tissue which the user of the ablation device does not intend or desire to irrigate, those irrigated portions of the patient's tissue may be ablated. Moreover, when the ablation device sprays the conductive fluid onto the patient's tissue, the conductive fluid may splatter, and the patient's tissue and the tip of the ablation device may not remain substantially irrigated or saturated throughout the ablation procedure. Consequently, the charge of electricity may not be continuously applied from the tip of the ablation device to the patient's tissue via the conductive fluid.

SUMMARY OF THE INVENTION

Therefore, a need has arisen for holders for ablation devices, surgical devices employing such holders, and methods of employing such surgical devices, that overcome these and other shortcomings of the related art. A technical advantage of the present invention is that a holder for an ablation device may be adapted to receive any known ablation device. Moreover, when the ablation device is disposed within the holder, the tip of the ablation device may not contact a patient's tissue during a surgical procedure involving ablation. Another technical advantage of the present invention is that the patient's tissue may be drawn inside a portion of the holder and may form a substantially airtight seal with an opening formed at an end of the holder. Consequently, when a conductive fluid is delivered to the patient's tissue, the conductive fluid only may be delivered to those portions of the patient's tissue drawn inside the holder, and the patient's tissue and the tip of the ablation device may remain substantially irrigated or saturated throughout the surgical procedure. Yet another technical advantage of the present invention is that portions of the ablated tissue which disseminate within the holder during ablation may be removed from the holder during the surgical procedure.

According to an embodiment of the present invention, a holder for an ablation device is described. The holder comprises an inner cavity having a first opening formed therethrough, in which the inner cavity is adapted to receive an ablation device. In one embodiment, the holder also may comprise a first outer cavity surrounding the inner cavity. Alternatively, the holder may comprise a tip portion having a second opening formed therethrough, in which the tip portion is formed at a first end of the holder and extends beyond the inner cavity, such that a reaction chamber is formed between the first opening and the second opening. In yet another embodiment, the holder may comprise a first outer cavity surrounding the inner cavity and a tip portion having a second opening formed therethrough. Moreover, in this embodiment, the tip portion may be formed at a first end of the holder and may extend beyond the inner cavity, such that a reaction chamber is formed between the first opening and the second opening.

According to another embodiment of the present invention, a surgical device is described. The surgical device comprises a holder for an ablation device, which includes an inner cavity having a first opening formed therethrough, in which the inner cavity is adapted to receive an ablation device. The surgical device also includes an ablation device disposed within the inner cavity. In one embodiment, the holder also may comprise a first outer cavity surrounding the inner cavity. Alternatively, the holder may comprise a tip portion having a second opening formed therethrough, in which the tip portion is formed at a first end of the holder and extends beyond the inner cavity, such that a reaction chamber is formed between the first opening and the second opening. In yet another embodiment, the holder may comprise a first outer cavity surrounding the inner cavity and a tip portion having a second opening formed therethrough. Moreover, in this embodiment, the tip portion may be formed at a first end of the holder and may extend beyond the inner cavity, such that a reaction chamber is formed between the first opening and the second opening.

According to yet another embodiment of the present invention, a method of performing a surgical procedure is described. The method comprises the step of disposing an ablation device within a holder, in which the holder comprises an inner cavity having a first opening formed therethrough, in which the inner cavity is adapted to receive the ablation device. The holder also comprises a tip portion having a second opening formed therethrough, in which the tip portion is formed at a first end of the holder and extends beyond the inner cavity, such that a reaction chamber is formed between the first opening and the second opening. The method also comprises the step of drawing at least a portion of a patient's tissue inside the reaction chamber, such that the patient's tissue forms a substantially air tight seal with the second opening. In one embodiment, the method further comprises the steps of irrigating the portion of the patient's tissue drawn inside said reaction chamber and ablating at least a portion of the patient's tissue drawn inside said reaction chamber. In this embodiment, the method also comprises the step of removing at least a portion of the patient's tissue which disseminated within the reaction chamber during the ablation of the patient's tissue.

BRIEF DESCRIPTION OF THE DRAWINGS

For a more complete understanding of the present invention, needs satisfied thereby, and objects, features, and advantages thereof, reference now is made to the following descriptions taken in connection with the accompanying drawings.

DETAILED DESCRIPTION OF PREFERRED EMBODIMENTS

Figure 1:
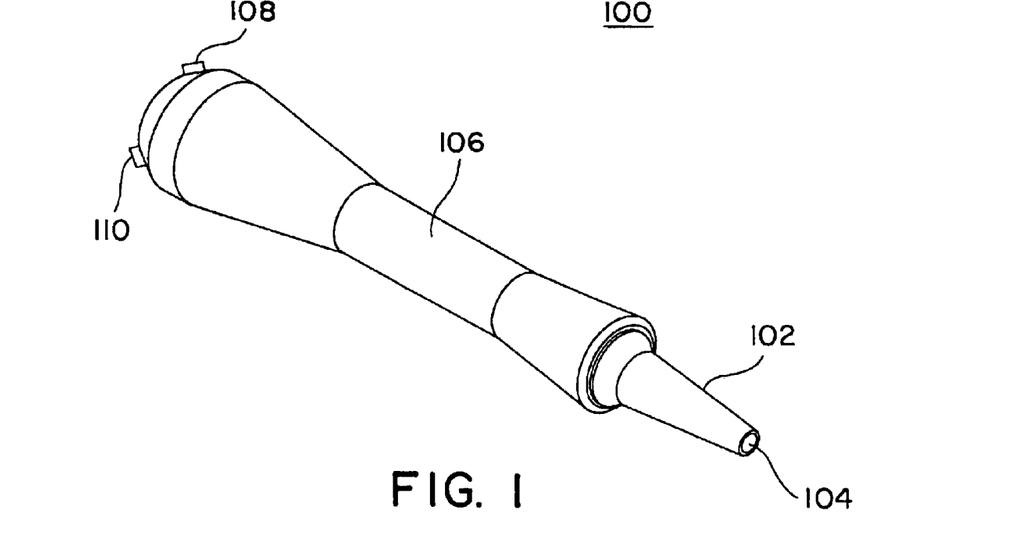
FIG. 1 is a perspective view of a holder for an ablation device according to an embodiment of the present invention.
Figure 2:
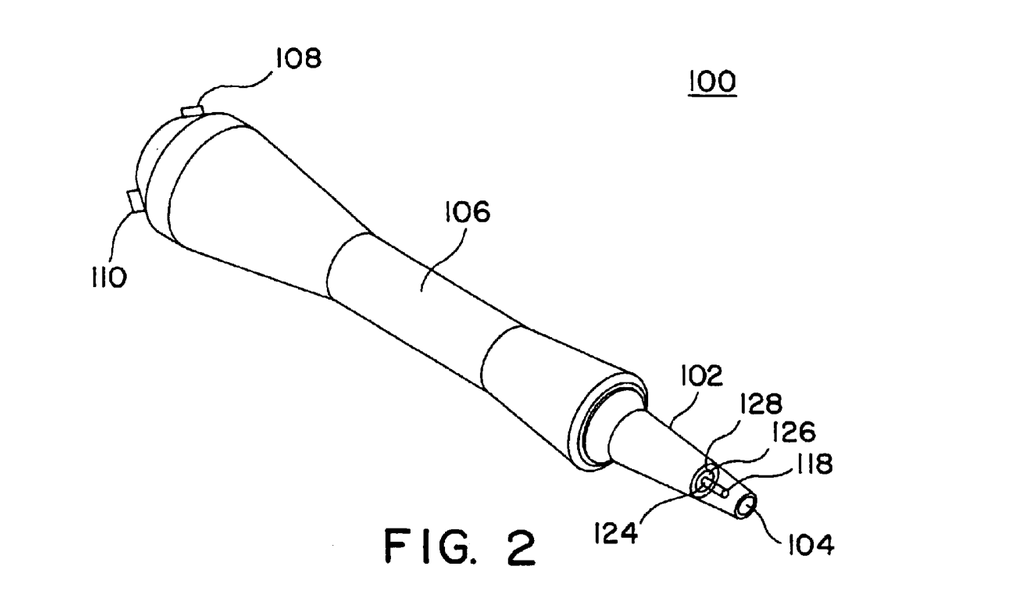
FIG. 2 is a perspective view of the holder of FIG. 1, depicting the inside of a tip portion of the holder and an ablation device disposed within the holder according to an embodiment of the present invention.
Figure 3A:
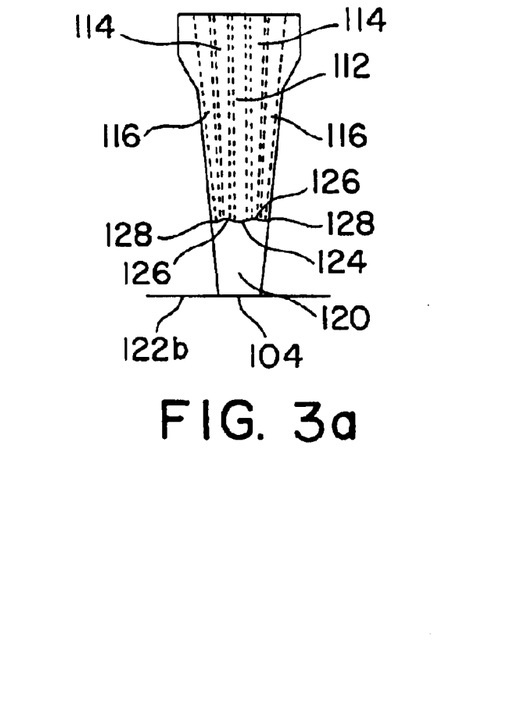
FIG. 3a is a cross-sectional side view of the tip portion of the holder of FIG. 1 according to an embodiment of the present invention.
Figure 3B:
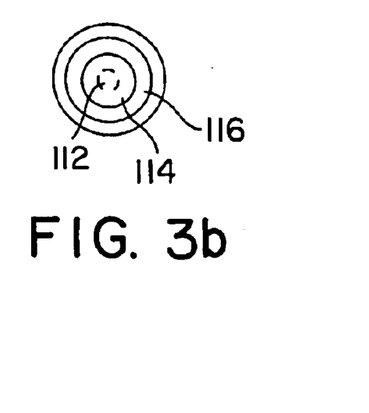
FIG. 3b is a cross-sectional top view of the tip portion of the holder of FIG. 1 according to an embodiment of the present invention.
Figure 3C:
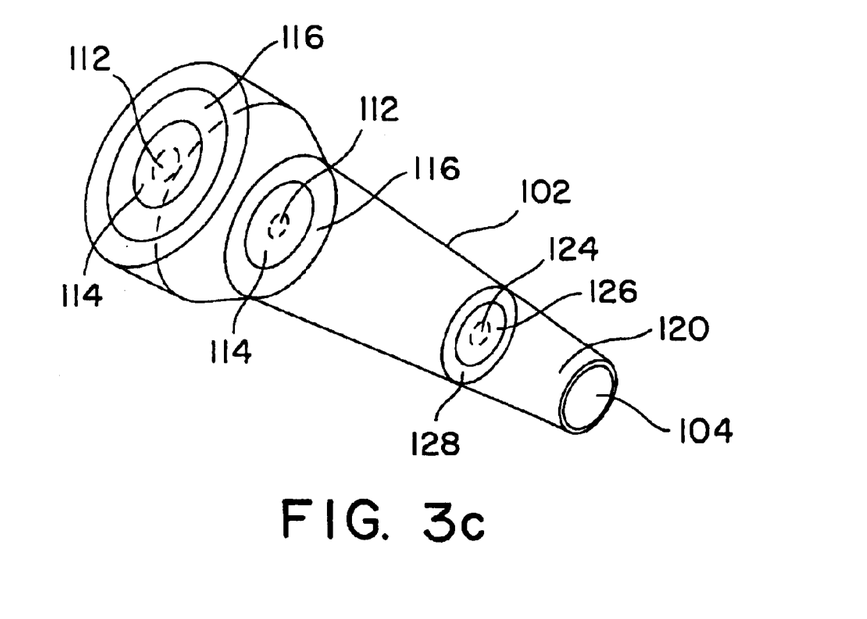
FIG. 3c is a cross-sectional perspective view of the tip portion of the holder of FIG. 1 according to an embodiment of the present invention.
Figure 4A:
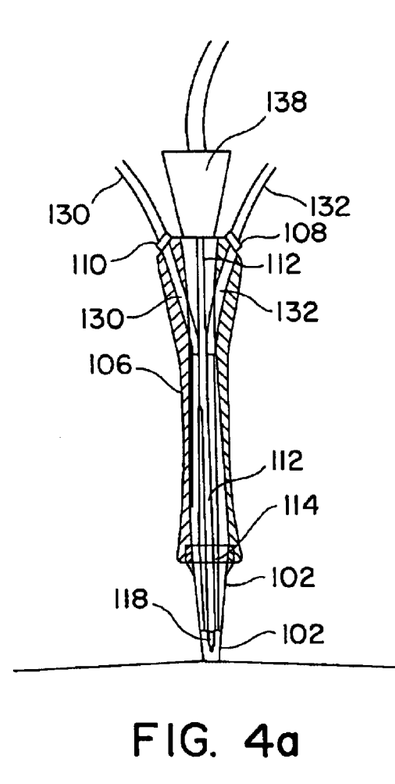
FIG. 4a is a cross-sectional side view of the holder of FIG. 1 including an ablation device disposed in the holder according to an embodiment of the present invention.
Figure 4B:
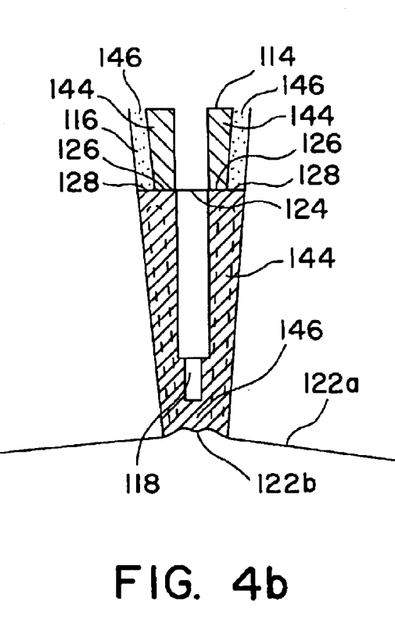
FIG. 4b is a cross-sectional side view of the holder of FIG. 1 according to an embodiment of the present invention.
Figure 5:
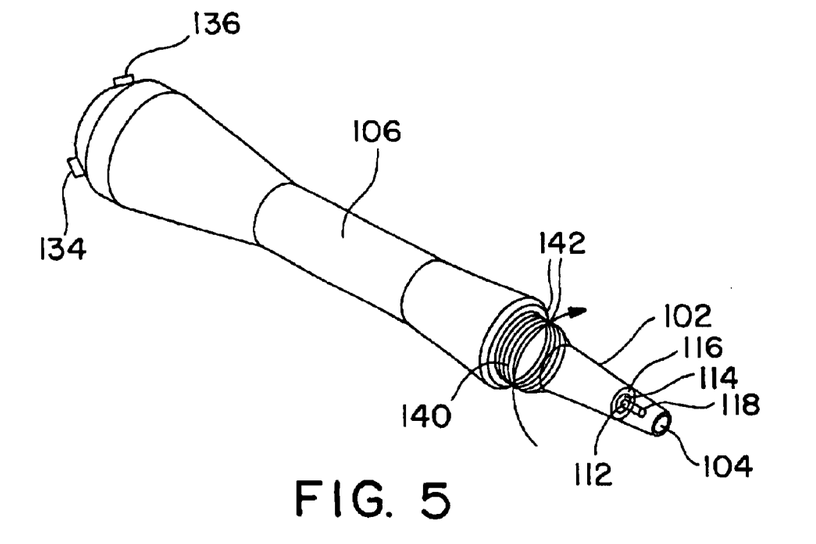
FIG. 5 is a perspective view of the holder of FIG. 2, depicting a means for adjusting the length of the tip portion according to an embodiment of the present invention.
Figure 6:
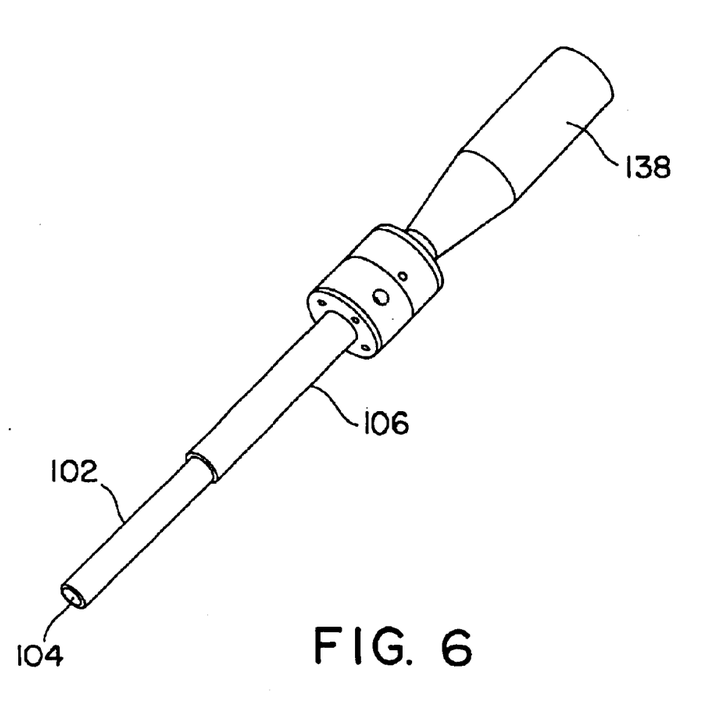
FIG. 6 is a perspective view of a holder for an ablation device including an ablation device disposed within the holder and having a different shape than the holder of FIG. 1 according to an embodiment of the present invention.
Figure 7:
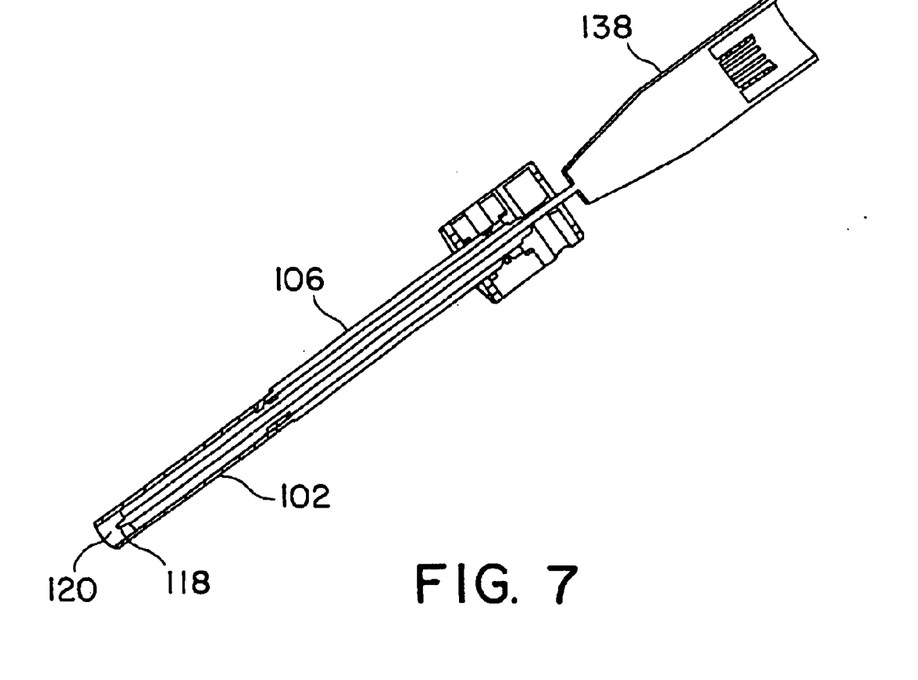
FIG. 7 is a cross-sectional perspective view of the holder of FIG. 6 according to an embodiment of the present invention.
Figure 8:
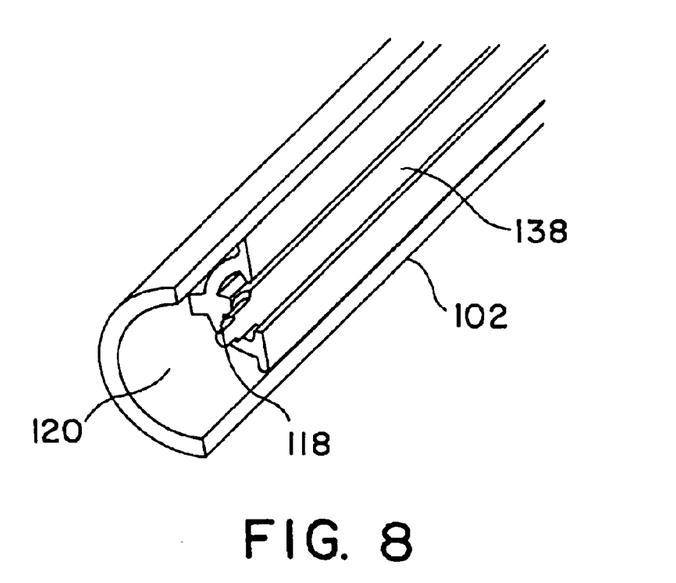
FIG. 8 is a cross-sectional perspective view of a tip of the holder of FIG. 6 according to an embodiment of the present invention.
Figure 9:
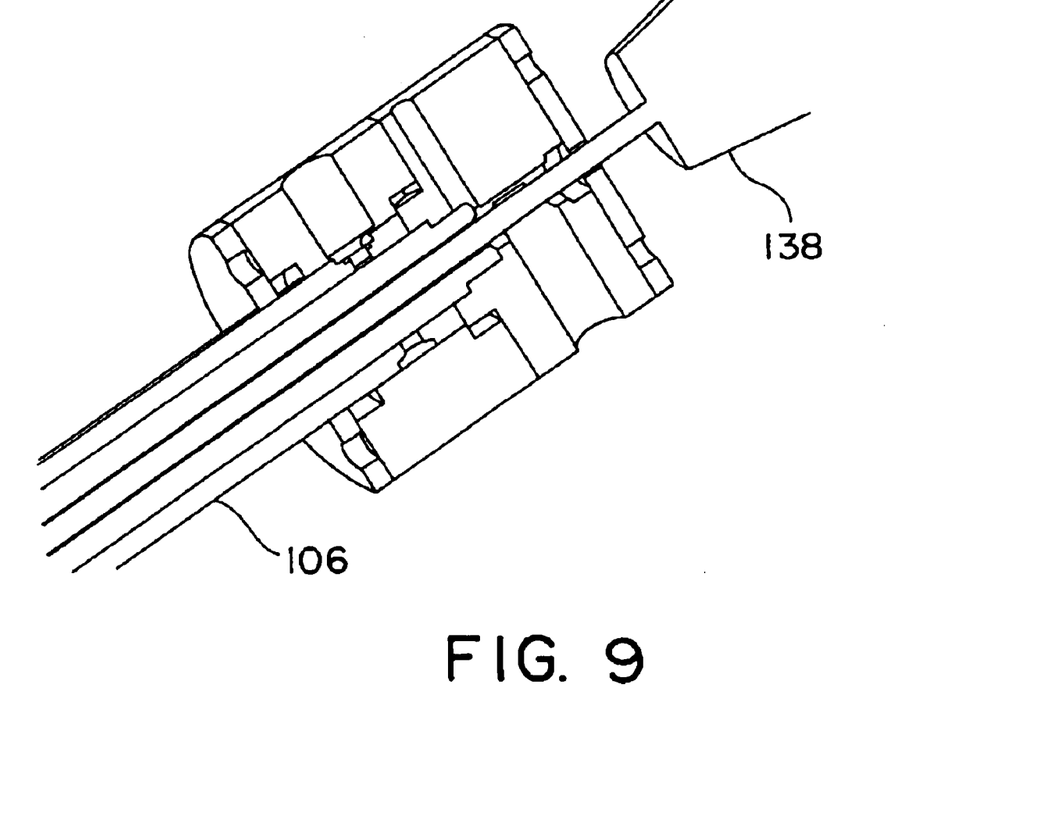
FIG. 9 is a cross-sectional perspective view of a shaft of the holder of FIG. 6 according to an embodiment of the present invention.

Preferred embodiments of the present invention and their advantages may be understood by referring to FIGS. 1–9, like numerals being used for like corresponding parts in the various drawings.

Referring to FIGS. 1–9, a holder 100 for an ablation device 138 is described. Holder 100 may comprise an inner cavity 112, which may have an opening 124 formed therethrough, such that inner cavity 112 may be adapted to receive any known ablation device 138. For example, inner cavity 112 may be adapted to receive ablation device 138, such as an ablation device described in U.S. Pat. No. 5,871,469 to Eggers et al., U.S. Pat. No. 5,697,909 to Eggers et al., U.S. Pat. No. 5,697,882 to Eggers et al., U.S. Pat. No. 5,697,281 to Eggers et al., U.S. Pat. No. 5,681,282 to Eggers et al., U.S. Pat. No. 5,366,443 to Eggers et al., U.S. Pat. No. 6,063,081 to Mulier et al., U.S. Pat. No. 6,236,393 B1 to Mulier et al., or U.S. Pat. No. 6,277,115 B1 to Saadat, the disclosures of which are incorporated herein by reference. Nevertheless, it will be understood by those of ordinary skill in the art that inner cavity 112 may be adapted to receive any known ablation device.

In an embodiment, holder 100 also may comprise a first outer cavity 114, which may surround at least a portion of inner cavity 112. For example, first outer cavity 114 entirely may surround inner cavity 112, such that first outer cavity 114 may enclose inner cavity 112. Moreover, first outer cavity 114 may have an opening 126 formed therethrough. For example, opening 126 may be space or a gap between an exterior wall of inner cavity 112 and an interior wall of first outer cavity 114. In one embodiment, as shown by the broken lines in FIGS. 2, 3b, and 3c, inner cavity 112 may be eliminated or removed, such that first outer cavity 114 may be adapted to receive ablation device 138.

In any of the above-described embodiments of the present invention, holder 100 further may comprise a tip portion 102, which may have an opening 104 formed therethrough and also may be formed at a first end of holder 100. For example, tip portion 102 may enclose or surround at least a portion of inner cavity 112, and when first outer cavity 114 is present, also may enclose or surround at least a portion of first outer cavity 114. Moreover, a length of tip portion 102 may be selected such that tip portion 102 may extend beyond inner cavity 112. Similarly, the length of tip portion 102 may be selected such that tip portion 102 may extend beyond first outer cavity 114. When tip portion 102 extends beyond inner cavity 112 or first outer cavity 114, or both, a reaction chamber 120 may formed within tip portion 102, such that reaction chamber 120 may be formed between opening 104 and opening 124 or between opening 104 and opening 126, or both. In this embodiment, when ablation device 138 is disposed within inner cavity 112, at least a portion of ablation device 138, e.g., a tip 118 of ablation device 138 comprising at least one active electrode (not shown), may be positioned inside reaction chamber 120 via opening 124. In another embodiment, tip 118 may not extend outside reaction chamber 120, such that tip 118 may not contact a patient's tissue 122a drawn inside reaction chamber 120. In addition, tip portion 102 may be a tapered, substantially cylindrically shaped portion, such that a diameter of tip portion 102 may decrease towards opening 104. For example, the diameter of the portion of tip 102 comprising reaction chamber 120 may be about 0.375 inches. Tip portion 102 also may be a non-tapered, substantially cylindrically shaped portion, such that a diameter of tip portion 102 may be substantially constant.

In any of the above-described embodiments of the present invention, holder 100 also may comprise a second outer cavity 116, which may surround at least a portion of first outer cavity 114 and also may have an opening 128 formed therethrough. For example, second outer cavity 116 entirely may surround first outer cavity 114. In an embodiment when inner cavity 112 is removed and first outer cavity 114 is adapted to receive ablation device 138, first outer cavity 114 may be an inner cavity, and second outer cavity 116 may be a first inner cavity. Moreover, holder 100 may comprise means for drawing at least a portion of a target site 122a, e.g., a patient's tissue 122a, body part 122a, or the like, inside reaction chamber 120, which also may draw in at least a portion of ambient fluids (not shown) inside reaction chamber 120. For example, the means for drawing at least a portion of the patient's tissue 122a inside reaction chamber 120 may comprise a vacuum supply line 130, such as a controllable or a variable vacuum supply line. When the patient's tissue 122a, or ambient fluids and the patient's tissue 122a, are drawn inside reaction chamber 120, the patient's tissue 122a may form a substantially air tight seal with opening 104. Holder 100 also may comprise means for irrigating the portion of the patient's tissue 122a drawn inside reaction chamber 120, e.g., a controlled irrigation of the patient's tissue 122a. For example, the means for irrigating the portion of the patient's tissue 122a drawn inside reaction chamber 120 may comprise a conductive fluid supply line 132, which may deliver a conductive fluid 144, e.g., a saline solution or any other known conductive fluid, or the like, to the portion of the patient's tissue 122a drawn inside reaction chamber 120. Moreover, when the patient's tissue 122a forms a substantially air tight seal with opening 104, conductive fluid 144 may not escape tip portion 102 via opening 104. In an embodiment, at least a portion of vacuum supply line 130 may be in communication with, and positioned inside, at least a portion of inner cavity 112. Alternatively, at least a portion of vacuum supply line 130 may be in communication with, and positioned inside, at least a portion of first outer cavity 114 or second outer cavity 116. Similarly, in an embodiment, at least a portion of conductive fluid supply line 132 may be in communication with, and positioned inside, at least a portion of inner cavity 112. Alternatively, at least a portion of conductive fluid supply line 130 may be in communication with, and positioned inside, at least a portion of first outer cavity 114 or second outer cavity 116. Moreover, vacuum supply line 130 and conductive fluid supply line 132 may be positioned substantially opposite each other. Nevertheless, in yet another embodiment, vacuum supply line 130 or conductive fluid supply line 132, or both, may be in communication with, but positioned outside, cavities 112, 114, or 116, or any combinations thereof.

In any of the above-described embodiments of the present invention, holder 100 also may comprise a shaft 106, which may be connected to tip portion 102. In this embodiment, at least a portion of vacuum supply line 130 and at least a portion of conductive fluid supply line 132 may be in communication with, and positioned inside, shaft 106. Alternatively, vacuum supply line 130 or conductive fluid supply line 132, or both, may be in communication with, but positioned outside shaft 106. Moreover, at least a portion of inner cavity 112, at least a portion of first outer cavity 114, or at least a portion of second outer cavity 116, or any combinations thereof, may extend inside shaft 106, such that shaft 106 may enclose or surround cavities 112, 114, or 116, respectively. In an embodiment, cavities 112, 114, or 116, or any combinations thereof, may have the same shape inside shaft 106 as they have inside tip portion 102, i.e., cavities 112, 114, or 116, or any combinations thereof, may be continuous, substantially uniform cavities. As such, first outer cavity 114 may surround at least a portion of inner cavity 112 throughout their respective lengths, i.e., within shaft 106 and within tip portion 102. Similarly, second outer cavity 116 may surround at least a portion of inner cavity 112 or first outer cavity 114, or both, throughout their respective lengths. In another embodiment, cavities 112, 114, or 116, or any combinations thereof, may have a different shape inside shaft 106 as they have inside tip portion 102, i.e., cavities 112, 114, or 116, or any combinations thereof, may have a non-uniform shape. For example, those portions of cavities 112, 114, or 116, or any combinations thereof, formed within shaft 106 may be substantially cylindrical channels which may be positioned lengthwise within shaft 106, and also may communicate with those portions of cavities 112, 114, or 116, formed within tip portion 102. In this embodiment, the portion of first outer cavity 114 positioned inside shaft 106 may be positioned adjacent to, but may not surround, inner cavity 112. Similarly, the portion of second outer cavity 116 positioned inside shaft 106 may be positioned adjacent to, but may not surround, inner cavity 112 or first outer cavity 114, or both. In any of the above-described embodiments comprising shaft 106, holder 100 further may comprise a connector 108, which may connect or communicate conductive fluid supply line 132 with the portion of second outer cavity 116 formed within shaft 106. Alternatively, connector 108 may connect or communicate conductive fluid supply line 132 with the portion of first outer cavity 114 formed within shaft 106. Similarly, holder 100 also may comprise a connector 110, which may connect or communicate vacuum supply line 130 with the portion of first outer cavity 114 formed within shaft 106. Alternatively, connector 110 may connect or communicate vacuum supply line 130 with the portion of second outer cavity 116 formed within shaft 106. Moreover, shaft 106 may include at least one ventilation hole (not shown) formed therethrough. For example, the at least one ventilation hole may extend from the exterior surface of shaft 106 into the cavity 112, 114, or 116 in communication with vacuum supply line 130. In operation, a user may cover the at least one ventilation hole, e.g., by placing their finger over the ventilation hole, when the user wishes to maintain the seal between opening 104 and patient's tissue 122b. Nevertheless, in this embodiment, the user may break the seal between opening 104 and patient's tissue 122b by uncovering the at least one ventilation hole.

In any of the above-described embodiments of the present invention, holder 100 further may comprise means for adjusting a length of tip portion 102, i.e., means for adjusting a distance between opening 104 and opening 124. For example, the means for adjusting the distance between opening 104 and opening 124 may comprise a plurality of threads 142 formed on a threaded portion 140 of the exterior surface of tip portion 102. Moreover, threaded portion 140 may be formed adjacent to shaft 106, such that when tip portion 102 turns in a predetermined direction, tip portion 102 may be unscrewed, i.e., the distance between opening 104 and opening 124 may increase. Similarly, when tip portion 102 turns in a direction opposite the predetermined direction, tip portion 102 may move further inside shaft 106, i.e., the distance between opening 104 and opening 124 may decrease. In an embodiment, the distance between opening 104 and opening 124 may be adjusted between about 0.010 centimeters and about 2.000 centimeters. For example, the distance between opening 104 and opening 124 may be about 0.375 centimeters.

In any of the above-described embodiments of the present invention, holder 100 also may comprise at least one video capture device (not shown) positioned inside reaction chamber 120. For example, the video capture device may comprise a fiber optic camera (not shown). Moreover, in any of the above-described embodiments of the present invention, holder 100 further may comprise ablation device 138, which may be disposed within inner cavity 112, such that tip 118 of ablation device 138 may be positioned within reaction chamber 120. In addition, ablation device 138 may be removable from inner cavity 112. In this embodiment, the combination of holder 100 and ablation device 138 may be a surgical device, such that holder 100 and ablation device 138 may be used in combination in order to perform a surgical procedure, such as an ablation procedure.

In operation, and according to a method embodiment of the present invention, ablation device 138 may be disposed within a holder 100 according any of the above-described embodiments of the present invention, such that a tip 118 of ablation device 138 may be positioned within reaction chamber 120. Moreover, at least a portion of a patient's tissue 122a which a user wishes to perform a surgical procedure upon, such as an ablation procedure, may be drawn inside reaction chamber 120 and may form a substantially air tight seal with opening 104. When the patient's tissue 122a forms the substantially air tight seal with opening 104, those portions of the patient's tissue which the user does not wish to perform the surgical procedure upon, e.g., patient's tissue 122b, may not be drawn inside reaction chamber 120. Further, the patient's tissue 122a inside reaction chamber 120 may be irrigated with a conductive fluid 144 and a charge of electricity may be applied from tip 118 to tissue 122a via conductive fluid 144, such that tissue 122a may be ablated. For example, reaction chamber 120 may be substantially filled with conductive fluid 144 before tip 118 ablates tissue 122a, such that tip 118 and tissue 122a may remain substantially irrigated or saturated during the surgical procedure. Moreover, when the patient's tissue 122a forms the airtight seal with opening 104, conductive fluid 144 may not escape holder 100 via opening 104, such that patient's tissue 122b may not be irrigated. Consequently, the charge of electricity may not be applied from tip 118 to tissue 122b via conductive fluid 144, and tissue 122b may not be ablated. Further, when tissue 122a is ablated, at least a portion of tissue 122a may disseminate within reaction chamber 120, i.e., disseminated tissue particles 146. Nevertheless, in an embodiment, disseminated tissue particles 146 may be removed from reaction chamber 120 via vacuum supply line 130. When ablation of the patient's tissue 122a is completed, ablation device 138 may be removed from holder 100.

While the invention has been described in connection with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. It is intended that the specification and the described examples are considered as exemplary only, with the true scope and spirit of the invention indicated by the following claims.

I claim:

1. A holder for an ablation device comprising:
   an inner cavity having a first opening formed therethrough, wherein said inner cavity is adapted to receive an ablation device;
   a first outer cavity surrounding at least a portion of said inner cavity;
   a tip portion having a second opening formed through an end of said tip portion, wherein said tip portion extends beyond said inner cavity and said first outer cavity, such that a reaction chamber is formed between said first opening and said second opening;
   means for drawing at least a portion of patient's tissue inside said reaction chamber; and
   means for irrigating said portion of said patient's tissue drawn inside said reaction chamber.

2. The holder of claim 1, further comprising means for adjusting a distance between said first opening and said second opening.

3. The holder of claim 1, wherein when an ablation device is disposed within said inner cavity, at least a portion of said ablation device is positioned inside said reaction chamber and said ablation device is removable from said inner cavity.

4. The holder of claim 1, wherein when said patient's tissue is drawn inside said reaction chamber, said patient's tissue forms a substantially airtight seal with said second opening, wherein the means for drawing at least a portion of said patient's tissue inside said reaction chamber comprises a vacuum supply line, at least a portion of which is in communication with said inner cavity or said first outer cavity, and the means for irrigating said portion of said patient's tissue drawn inside said reaction chamber comprises a conductive fluid supply line, at least a portion of which is in communication with said inner cavity or said first outer cavity.

5. The holder of claim 1, wherein the means for drawing at least a portion of said patient's tissue inside said reaction chamber comprises a vacuum supply line, and the means for irrigating said portion of said patient's tissue drawn inside said reaction chamber comprises a conductive fluid supply line.

6. The holder of claim 5 further comprising a second outer cavity surrounding at least a portion of said first outer cavity.

7. The holder of claim 6, wherein at least a portion of said vacuum supply line is in communication with said first outer cavity or said second outer cavity, and at least a portion of said conductive fluid supply line is in communication with said first outer cavity or said second outer cavity.

8. The holder of claim 7, wherein said conductive fluid supply line is positioned substantially opposite said vacuum supply line.

9. The holder of claim 7, wherein said conductive fluid comprises a saline solution.

10. The holder of claim 7 further comprising a shaft comprising at least one ventilation hole, wherein said shaft is connected to said tip portion, and at least a portion of said vacuum supply line and at least a portion of said conductive fluid supply line are in communication with said shaft.

11. The holder of claim 1, wherein said reaction chamber has a diameter between about 0.1 inches and about 0.5 inches.

12. The holder of claim 1, further comprising a video capture device positioned inside said reaction chamber.

13. The holder of claim 12, wherein said video capture device comprises a fiber optic camera.

14. The holder of claim 1, wherein a distance between said first opening and said second opening is between about 0.010 centimeters and about 2.000 centimeters.

15. A holder for an ablation device comprising:
   an inner cavity having a first opening formed therethrough, wherein said inner cavity is adapted to receive an ablation device;
   a tip portion having a second opening formed through an end of said tip portion, wherein said tip portion extends beyond said inner cavity, such that a reaction chamber is formed between said first opening and said second opening;
   means for drawing at least a portion of a patient's tissue inside said reaction chamber; and
   means for irrigating said portion of said patient's tissue drawn inside said reaction chamber.

16. The holder of claim 15 further comprising a first outer cavity surrounding at least a portion of said inner cavity, wherein said tip portion encloses at least a portion of said inner cavity and at least a portion of said first outer cavity.

17. The holder of claim 16 further comprising means for adjusting a distance between said first opening and said second opening.

18. The holder of claim 16, wherein when said patient's tissue is drawn inside said reaction chamber, said patient's tissue forms a substantially airtight seal with said second opening, wherein the means for drawing at least a portion of said patient's tissue inside said reaction chamber comprises a vacuum supply line, at least a portion of which is in communication with said inner cavity or said first outer cavity, and the means for irrigating said portion of said patient's tissue drawn inside said reaction chamber comprises a conductive fluid supply line, at least a portion of which is in communication with said inner cavity or said first outer cavity.

19. The holder of claim 16, wherein the means for drawing at least a portion of said patient's tissue inside said reaction chamber comprises a vacuum supply line, and the means for irrigating said portion of said patient's tissue drawn inside said reaction chamber comprises a conductive fluid supply line.

20. The holder of claim 19 further comprising a second outer cavity surrounding at least a portion of said first outer cavity.

21. The holder of claim 20, wherein at least a portion of said vacuum supply line is in communication with said first outer cavity or said second outer cavity, and at least a portion of said conductive fluid supply line is in communication with said first outer cavity or said second outer cavity.

22. A surgical device comprising:
a holder for an ablation device, wherein said holder comprises:
an inner cavity having a first opening formed therethrough, wherein said inner cavity is adapted to receive an ablation device; and
a first outer cavity surrounding at least a portion of said inner cavity;
a tip portion having a second opening formed through an end of said tip portion, wherein said tip portion extends beyond said inner cavity and said first outer cavity, such that a reaction chamber is formed between said first opening and said second opening;
means for drawing at least a portion of a patient's tissue inside said reaction chamber; and
means for irrigating said portion of said patient's tissue drawn inside said reaction chamber; and
an ablation device disposed within said inner cavity.

23. The surgical device of claim 22, wherein said holder further comprises means for adjusting a distance between said first opening and said second opening.

24. The surgical device of claim 22, wherein at least a portion of said ablation device is positioned inside said reaction chamber, and said ablation device is removable from said inner cavity.

25. The surgical device of claim 22, wherein when said patient's tissue is drawn inside said reaction chamber, said patient's tissue forms a substantially airtight seal with said second opening.

26. The surgical device of claim 22, wherein the means for drawing at least a portion of said patient's tissue inside said reaction chamber comprises a vacuum supply line, and the means for irrigating said portion of said patient's tissue drawn inside said reaction chamber comprises a conductive fluid supply line.

27. The surgical device of claim 26, wherein said holder further comprises a second outer cavity surrounding at least a portion of said first outer cavity.

28. The surgical device of claim 27, wherein at least a portion of said vacuum supply line is in communication with said first outer cavity or said second outer cavity, and at least a portion of said conductive fluid supply line is in communication with said first outer cavity or said second outer cavity.

29. The surgical device of claim 22, wherein at least a portion of said ablation device is positioned inside said reaction chamber.

30. The surgical device of claim 29, wherein said portion of said ablation device positioned inside said reaction chamber and said patient's tissue do not contact during a surgical procedure.

31. A surgical device comprising:
a holder for an ablation device, wherein said holder comprises:
an inner cavity having a first opening formed therethrough, wherein said inner cavity is adapted to receive an ablation device;
a tip portion having a second opening formed through an end of the tip portion, wherein said tip portion extends beyond said inner cavity, such that a reaction chamber is formed between said first opening and said second opening;
means for drawing at least a portion of a patient's tissue inside said reaction chamber; and
means for irrigating said portion of said patient's tissue drawn inside said reaction chamber
an ablation device disposed within said inner cavity.

32. The surgical device of claim 31, wherein said holder further comprises a first outer cavity surrounding at least a portion of said inner cavity, wherein said tip portion encloses at least a portion of said inner cavity and at least a portion of said first outer cavity, wherein said ablation device is removable from said inner cavity.

33. The surgical device of claim 32, wherein said holder further comprises means for adjusting a distance between said first opening and said second opening.

34. The surgical device of claim 32, wherein at least a portion of said ablation device is positioned inside said reaction chamber, and said ablation device is removable from said inner cavity.

35. The surgical device of claim 32, wherein when said patient's tissue is drawn inside said reaction chamber, said patient's tissue forms a substantially airtight seal with said second opening.

36. The surgical device of claim 32, wherein the means for drawing at least a portion of said patient's tissue inside said reaction chamber comprises a vacuum supply line, and the means for irrigating said portion of said patient's tissue drawn inside said reaction chamber comprises a conductive fluid supply line.

37. The surgical device of claim 36, wherein said holder further comprises a second outer cavity surrounding at least a portion of said first outer cavity.

38. The surgical device of claim 37, wherein at least a portion of said vacuum supply line is in communication with said first outer cavity or said second outer cavity, and at least a portion of said conductive fluid supply line is in communication with said first outer cavity or said second outer cavity.

39. The surgical device of claim 38, wherein at least a portion of said ablation device is positioned inside said reaction chamber.

40. The surgical device of claim 39, wherein said portion of said ablation device positioned inside said reaction chamber and said patient's tissue do not contact during a surgical procedure.

41. A method of performing a surgical procedure comprising the steps of:

(a) disposing an ablation device within a holder, wherein said holder comprises:
  an inner cavity having a first opening formed therethrough, wherein said inner cavity is adapted to receive said ablation device; and
  a tip portion having a second opening formed through an end of the tip portion, wherein said tip portion extends beyond said inner cavity, such that a reaction chamber is formed between said first opening and said second opening,
(b) drawing at least one portion of a patient's tissue inside said reaction chamber; and
(c) after the performance of step (b), irrigating said at least one portion of said patient's tissue.

42. The method of claim 41 further comprising the steps of:

ablating said at least one portion of said patient's tissue drawn inside said reaction chamber; and removing at least a portion of said patient's tissue which disseminates within said reaction chamber during said ablation of said patient's tissue.

43. The method of claim 42, wherein the step of irrigating said portion of said patient's tissue drawn inside said reaction chamber comprises the step of maintaining conductive fluid inside said reaction chamber throughout said ablation of said patient's tissue.

44. The method of claim 42 further comprising the steps of removing said ablation device from said inner cavity when ablation of said patient's tissue is complete.

* * * * *